US00PP12479P2

(12) United States Plant Patent
Noodelijk

(10) Patent No.: US PP12,479 P2
(45) Date of Patent: Mar. 19, 2002

(54) CHRYSANTHEMUM NAMED 'ODIN'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/562,275

(22) Filed: May 1, 2000

(51) Int. Cl.[7] ..... A01H 5/00

(52) U.S. Cl. ..... Plt./294

(58) Field of Search ..... Plt./294

*Primary Examiner*—Bruce R. Campell
*Assistant Examiner*—Annette H. Para
(74) *Attorney, Agent, or Firm*—Parkhurst & Wendel, LLP

(57) ABSTRACT

A chrysanthemum plant named 'ODIN' characterized by its medium sized blooms with white ray florets and prolific branching; natural season flower date 12–17 August; blooming for a period of 5 weeks.

2 Drawing Sheets

BACKGROUND OF THE INVENTION

'ODIN' is a product of a breeding and selection program for outdoor pot mums (garden mums) which had the objective of creating new chrysanthemum cultivars with a daisy type flower, a natural season flower date around 12–17 August ; blooming for a period of 5 weeks. The new plant of the present invention comprises a new and distinct cultivar of Chrysanthemum plant 'ODIN' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in August 1996. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
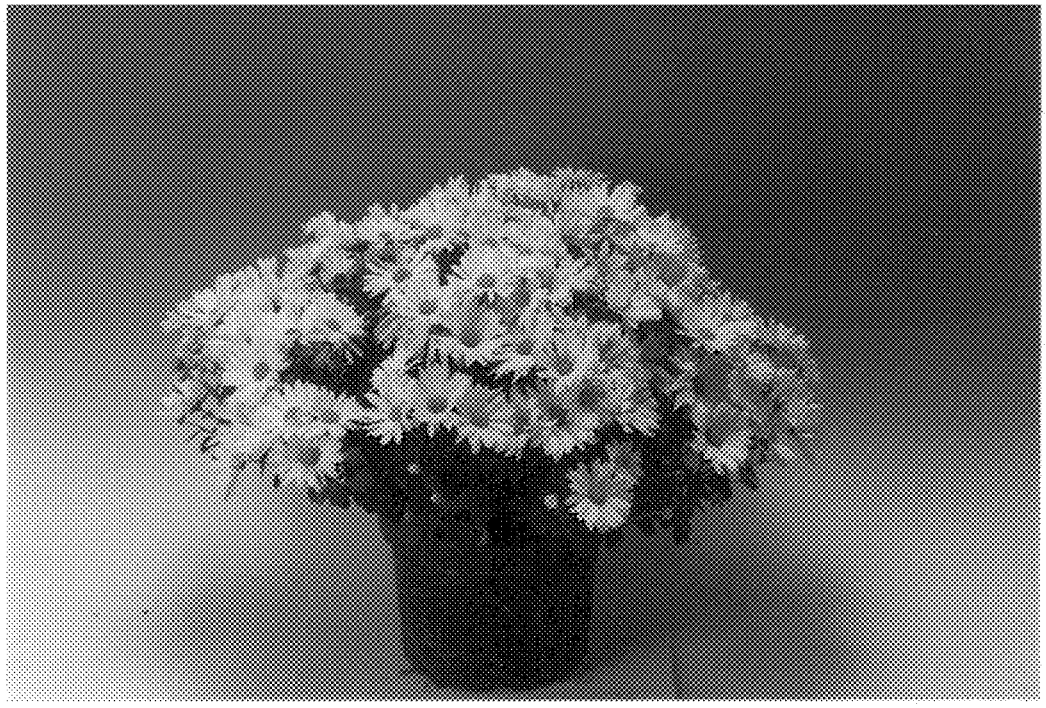
FIG. 1 shows a plant of the cultivar in full bloom.
Figure 2:
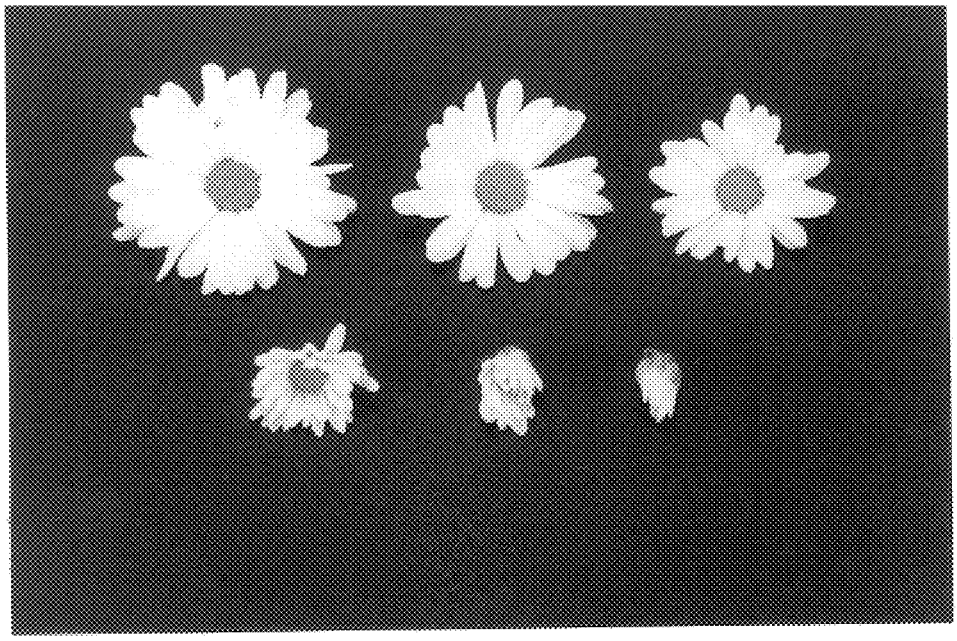
FIG. 2 shows the various stages of bloom of the new cultivar.
Figure 3:
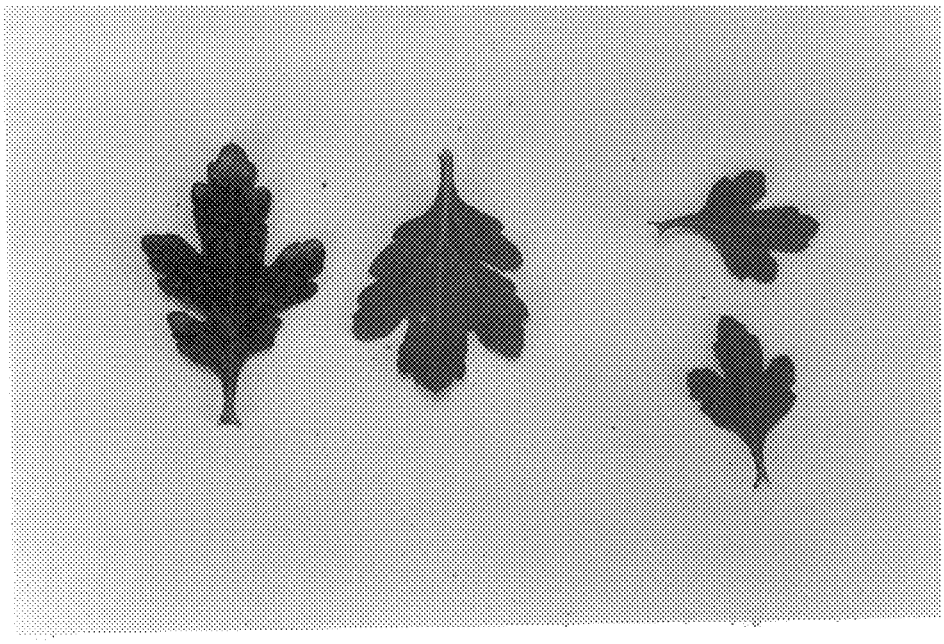
FIG. 3 shows the various stages of foliage and petiole of the new cultivar.

This new variety of chrysanthemum is of the botanical classification *dendranthema grandiflora*. The observations and measurements were gathered from 11 weeks old plants grown out door in Rijsenhout, Holland under natural day length and temperature and planted week 22 in 1997 and 1998. The natural blooming date of this crop was 12–17 August (week 33). The plants were observed (directly) during the flowering of this crop. The average height of the plants was 28–32 cms. No growth retardants were used. No tests were done on cold or drought tolerance. This new variety produces medium sized blooms with white ray florets and yellow disc florets (when visible).

From the cultivars known to inventor the most similar existing cultivar in comparison to 'ODIN' is 'STEPHANIE' (U.S. Plant Pat. No. 9,445). When 'STEPHANIE' and 'ODIN' are being compared the following differences are noticed: The differences of 'STEPHANIE' and 'ODIN' are (1) natural flowering date. 'ODIN' flowers earlier. (2) flower color. 'ODIN' has a more pure white flower.

The following is a description of the plant and characteristics that distinguish 'ODIN' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, edition 1995.

Botanical Classification

*Dendranthema grandiflora* 'ODIN'

Bud:
- *Size.*—Medium, cross-section 1.2 cm. height 1.1 cm.
- *Outside color.*—Yellow-white 158 D.
- *Involucral bracts.*—2 rows, length 7 mm, width 3 mm.
- *Involucral bracts among disc-florets.*—Not present.
- *Involucral bracts color.*—Green 137 A.

Bloom:
- *Type.*—Single.
- *Height.*—Flat.
- *Size.*—Medium.
- *Fully expanded.*—6.0 cm.
- *Number of blooms per branch.*—Approx. 5 blooms per branch.
- *Performance on the plant.*—5 weeks.
- *Seeds.*—Not produced.
- *Fragrance.*—Typical chrysanthemum.

Color:
- *Center of flower.*—Immature yellow-orange 15 C. Mature yellow 13 A.
- *Color of the upper surface of the ray-florets.*—White 155 D.
- *Color of the lower surface of the ray-florets.*—Yellow-white 158 D.

*Tonality from distance.*—A mounded garden mum with white daisy flowers and yellow disc florets.
*Discoloration to color.*—None.

Ray florets:
*Texture.*—Upper side and under side smooth.
*Number.*—24–26.
*Cross-section.*—Concave.
*Longitudinal axis of the majority.*—Straight, outer row reflexing.
*Length of corolla tube.*—Short.
*Ray-floret margin.*—Entire.
*Ray-floret length.*—2.4–2.7 cm.
*Ray-floret width.*—0.7–0.8 cm.
*Ratio length / width.*—High.
*Shape of tip.*—Rounded.

Disc florets:
*Disc diameter.*—1.0 cm.
*Distribution of disc florets.*—Numerous, clearly visible at all stages of flowering.
*Shape.*—Tubular.
*Color.*—Yellow-orange 15 C.
*Receptacle shape.*—Conical raised.

Reproductive organs:
*Stamen* (*present in disc floret only*).—Yellow, thick, 3 mm in length.
*Stamen color.*—Yellow-orange 15 C.
*Pollen.*—Present, abundant.
*Pollen color.*—Yellow-orange 15 A.
*Styles.*—Thin.
*Style color.*—Yellow-green 144B.
*Style length.*—4 mm.
*Stigmas.*—Yellow-orange 15 C.
*Stigma width.*—2 mm.
*Ovaries.*—Enclosed in calyx.

Plant:
*Type.*—A garden mum (pot mum) meant for out door use.
*Growth habit.*—Spreading.
*Growth rate.*—Moderate.
*Height.*—28–32 cm.
*Width.*—30–32 cm.
*Stem color.*—Green 137 A.
*Stem strength.*—Weak.
*Stem brittleness.*—Absent.
*Stem anthocyanin coloration.*—Absent.
*Length of lateral branch.*—From top to bottom 13–14 cm.
*Lateral branch color.*—Green 137 A.
*Lateral branch, attachment.*—Weak.
*Branching* (*average number of lateral branches*).—Prolific with 7–9 breaks after pinching.
*Peduncle length.*—2.5–3.5 cm.
*Peduncle color.*—Green 137 A.
*Natural season blooming date.*—12–17 August.

Foliage:
*Color.*—Upper side green 139 A. Under side green 137 A.
*Size.*—Small, length 6.0 cm width 5.0 cm.
*Quantity* (*number per lateral branch*).—12–15.
*Shape.*—Oval.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Round.
*Margin of sinus between lateral lobes.*—Diverging.
*Shape of base.*—Attenuate.
*Apex.*—Mucronate.

Differences with the comparison varieties

| | 'ODIN' | 'STEPHANIE' |
|---|---|---|
| Natural flowering dat | 12–17 August | 18 September |
| Color ray-floret | White 155 D | White 155 B |

I claim:

1. A new and distinct variety of chrysanthemum plant as described and illustrated.

* * * * *